(12) United States Patent
Khan et al.

(10) Patent No.: US 6,826,520 B1
(45) Date of Patent: Nov. 30, 2004

(54) METHOD OF UPSCALING PERMEABILITY FOR UNSTRUCTURED GRIDS

(75) Inventors: Sameer A. Khan, Sugar Land, TX (US); Aaron G. Dawson, The Woodlands, TX (US)

(73) Assignee: ExxonMobil Upstream Research Company, Houston, TX (US)

( * ) Notice: Subject to any disclaimer, the term of this patent is extended or adjusted under 35 U.S.C. 154(b) by 961 days.

(21) Appl. No.: 09/593,121

(22) Filed: Jun. 13, 2000

Related U.S. Application Data (60) Provisional application No. 60/140,700, filed on Jun. 24, 1999.

(51) Int. Cl.⁷ ................................................ G06G 7/48
(52) U.S. Cl. ................................. 703/10; 703/9; 703/6; 702/6; 702/12; 702/9; 367/72; 166/335
(58) Field of Search .................................. 703/10, 2, 5

(56) References Cited

U.S. PATENT DOCUMENTS

| | | | | |
|---|---|---|---|---|
| 4,969,130 | A | | 11/1990 | Wason et al. .................. 367/73 |
| 5,710,726 | A | * | 1/1998 | Rowney et al. ................ 703/10 |
| 5,740,342 | A | | 4/1998 | Kocberber ..................... 395/120 |
| 5,757,663 | A | * | 5/1998 | Lo et al. .......................... 702/6 |
| 5,886,702 | A | | 3/1999 | Migdal et al. ............... 345/423 |
| 6,018,497 | A | * | 1/2000 | Gunasekera .................. 367/72 |
| 6,052,520 | A | * | 4/2000 | Watts, III ..................... 703/10 |
| 6,078,869 | A | * | 6/2000 | Gunasekera .................... 702/6 |
| 6,094,619 | A | * | 7/2000 | Noetinger et al. ............ 702/12 |
| 6,106,561 | A | * | 8/2000 | Farmer ......................... 703/10 |
| 6,230,101 | B1 | * | 5/2001 | Wallis .......................... 702/16 |

OTHER PUBLICATIONS

"Flexable Streamline Grids for Reservoir Simulation", M.G. Edwards, Stanford University—Petroleum Engineering Dept., Oct. 1998.*

P. Quandalle et al., "Reduction of Grid Effects Due to Local Sub–Gridding in Simulations Using a Composite Grid", Society of Petroleum Engineers, SPE 13527 (Feb. 10–13, 1985); pp. 295–301, 8 Figs., 1 Appendix, 2 Tables.

C.D. White et al., "Computing Absolute Transmissibility in the Presence of Fine–Scale Heterogeneity", Society of Petroleum Engineers, SPE 16011 (Feb. 1–4, 1987); pp. 209–220.

(List continued on next page.)

*Primary Examiner*—Kevin J. Teska
*Assistant Examiner*—Fred Ferris (57) ABSTRACT

A method is provided for scaling up permeabilities associated with a fine-scale grid of cells representative of a porous medium to permeabilities associated with an unstructured coarse-scale grid of cells representative of the porous medium. An areally unstructured, Voronoi, computational grid is generated using the coarse-scale grid as the genesis of the computational grid. The computational grid is then populated with permeabilities associated with the fine-scale grid. Flow equations are developed for the computational grid, the flow equations are solved, and inter-node fluxes and pressure gradients are then computed for the computational grid. These inter-node fluxes and pressure gradients are used to calculate inter-node average fluxes and average pressure gradients associated with the coarse-scale grid. The inter-node average fluxes and average pressure gradients associated with the coarse grid are then used to calculate upscaled permeabilities associated with the coarse-scale grid.

28 Claims, 7 Drawing Sheets

OTHER PUBLICATIONS

Sait Kocberber, "A Finite–Element Black Oil Simulation System for Heterogeneous Reservoirs With Horizontal Wells Having Vertical Hydraulic Fractures", Society of Petroleum Engineers, SPE 25269 (Feb. 28, 1993–Mar. 3, 1993); pp. 423–433.

Sait Kocberber, "The Modeling of Deviated Wells and Sloping Faults With Locally Unstructured Grids: Part 1—Gridding Aspects", Society of Petroleum Engineers, SPE 26506 (Oct. 3–6, 1993); pp. 885–886.

Sait Kocberber, "An Automatic Unstructured Grid Generation System for Geologically Complex Reservoirs", Society of Petroleum Engineers, SPE 28245 (Jul. 31, 1994–Aug. 3, 1994); pp. 225–240.

Naji Saad et al., "Effective Relative Permeability in Scale–Up and Simulation", Society of Petroleum Engineers, SPE 29592 (Mar. 20–22, 1995); pp. 451–464.

L. J. Durlofsky et al., "Scale Up of Heterogeneous Three Dimensional Reservoir Descriptions", Society of Petroleum Engineers, SPE 30709, SPE Journal, Sep. 1996; pp. 313–326.

Jaedong Lee et al., "Development and Application of a New Upscaling Technique", Society of Petroleum Engineers, SPE 30712, Oct. 22–25, 1995; pp. 89–101.

Arun T. A. Kumar et al., "Impacts of Scale–up on Fluid Flow from Plug to Gridblock Scale in Reservoir Rock", Society of Petroleum Engineers, SPE/DOE 35452, Apr. 21–24, 1996; pp. 517–532.

Thomas A. Hewett et al., "Scale–Averaged Effective Flow Properties for Coarse–Grid Reservoir Simulation", Society of Petroleum Engineers, SPE 37988, Jun. 8–11, 1997; pp. 127–135.

D. Gunasekera et al., "The Generation and Application of K–Orthogonal Grid Systems", Society of Petroleum Engineers, SPE 37998, Jun. 8–11, 1997; pp. 199–214.

M. L. Litvak et al., "Integrated Reservoir and Surface Pipeline Network Compositional Siumlations", Society of Petroleum Engineers, SPE 48859, Nov. 2–6, 1998; pp. 297–305.

Michael G. Edwards, "Split Tensor Operators Coupled with Quasi K–Orthogonal Grids", Society of Petroleum Engineers, SPE 51903, Feb. 14–17, 1999; pp. 243–252.

Yann Gautier et al., "Nested Gridding and Streamline–Based Simulation for Fast Reservoir Performance Prediction", Society of Petroleum Engineers, SPE 51931, Feb. 14–17, 1999; pp. 403–412.

Koichi Suzuki et al., "Scale–Up of Relative Permeabilities of Isolated Gridblocks Accounting for Boundary Effects", Society of Petroleum Engineers, SPE 51938, Feb. 14–17, 1999; pp. 441–449.

J. E. Warren et al., "Flow in Heterogenous Porous Media", Society of Petroleum Engineers Journal, Sep. 1961; pp. 153–169.

S. H. Begg et al., "Assingning Effective Values to Simulator Gridblock Parameters for Heterogenous Reservoirs", SPE Reservoir Engineering, Nov. 1989; pp. 455–463.

D. Li et al., "Global Scale–Up of Reservoir Model Permeability With Local Grid Refinement", Journal of Pertroleum Science and Engineering 14 (1995); pp. 1–13.

Dachang Li et al., "Scaleup of Reservoir–Model Relative Permeability With a Global Method", SPE Reservoir Engineering, Aug. 1996; pp. 149–157.

Donald W. Peaceman, "Effective Transmissibilities of a Gridblock by Upscaling–Comparison of Direct Methods with Renormalization", SPE Journal, vol. 2, SPE 36722, Sep. 1997; pp. 338–349.

Gillian E. Pickup, "Two–Phase Flow Upscaling for 3D Sedimentary Structures", 5th European Conference on the Mathematics of Oil Recovery, Leoben, Austria, Sep. 3–6, 1996; pp. 465–473.

Xian–Huan Wen et al., "Upscaling Hydraulic Conductivities in Heterogeneous Media: An Overview", Journal of Hydrology 183 (1996); pp. ix–xxxii.

M. A. Christie, "Upscaling for Reservoir Simulation", JPT, Nov. 1996; pp. 1004–1008.

G. E. Pickup et al., "Permeability Tensors for Sedimentary Structures", Mathematical Geology, vo. 26, No. 2, 1994; pp. 227–250.

Xiao–Hui Wu et al., "Analysis of Upscaling Absolute Permeability", Computational Geosciences 0 (1998); pp. 1–21.

Sait Kocberber, "An Automatic, Unstructured Grid–Generation System for Geologically Complex Reservoirs", SPE Computer Applications, Oct. 1995; pp. 105–111.

Dimitri J. Mavriplis, "Adaptive Mesh Generation for Viscous Flows Using Delaunay Triangulation", Journal of Computational Physics 90 (1990); pp. 271–291.

S. Rebay, "Efficient Unstructured Mesh Generation by Means of Delaunay Triangulation and Bowyer–Watson Algorithm", Journal of Computational Physics 106 (1993); pp. 125–138.

D. F. Watson, "Computing the $\eta$–Dimensional Delaunay Tessellation With Application to Voronoi Polytopes", The Computer Journal, vol. 24, No. 2, 1981; pp. 167–172.

H. Hin et al., "Generation of Unstructured Tetrahedral Meshes by Advancing Front Technique", International Journal for Numerical Methods in Engineering, vol. 36 (1993); pp. 1805–1823.

C. L. Palagi et al., "Use of Voronoi Grid in Reservoir Simulation", Society of Petroleum Engineers, SPE 22889 (Oct. 6–9, 1991; pp. 77–92.

Yoram Rubin et al., "A Stochastic Approach to the Problem of Upscaling of Conductivity in Disordered Media: Theory and Unconditional Numerical Simulations", Water Resources Research, vol. 26, No. 4 (Apr. 1990); pp. 691–701.

Huang et al. Yuantu. A Practical Fuzzy Interpolator for Prediction of Reservoir Permeability. Fuzzy Systems Conference Proceedings. Fuzz–IEEE '99. IEEE International. 1999 vol. 3. pp. 1528–1533.

Wong et al. P.M. An Improved Technique In Porosity Predition: A Neural Network Approach. IEEE Transactions on Geoscience and Remote Sensing. vol. 33. No. 4. Jul. 1995. pp. 971–980.

Nielson. D.L. Rock Permeability in High–Temperature Geothermal Systems. Proceedings of the 32nd Intersociety Energy Conversion Engineering Conference, IECEC–97. 1997. vol. 3. pp. 1837–1839.

Huang et al. Y. An Improved Fuzzy Neural Network for Permeability Estimation from Wireline Logs in a Petroleum Reservoir. TENCON '96. Proceedings. 1996 IEEE TENCON. Digital Signal Processing Applications. vol. 2. pp. 912–917.

Silver et al. D. Tracking Scalar Features in Unstructured Data Sets. Visualization '98 Proceedings. 1998. pp. 79–86.

* cited by examiner

METHOD OF UPSCALING PERMEABILITY FOR UNSTRUCTURED GRIDS

REFERENCE TO RELATED APPLICATIONS

This application claims the benefit of U.S. Provisional Application No. 60/140,700 filed Jun. 24, 1999.

FIELD OF THE INVENTION

This invention relates generally to simulating fluid flow in a porous medium and, more specifically, to a flow-based method of scaling-up permeability associated with a fine-grid system representative of the porous medium to permeability associated with a coarse-grid system also representative of the porous medium.

BACKGROUND OF THE INVENTION

Numerical simulation is widely used in industrial fields as a method of simulating a physical system by using a computer. In most cases, there is a desire to model the transport processes occurring in the physical systems. What is being transported is typically mass, energy, momentum, or some combination thereof. By using numerical simulation, it is possible to reproduce and observe a physical phenomenon and to determine design parameters without actual laboratory experiments or field tests. It can be expected therefore that design time and cost can be reduced considerably.

One type of simulation of great interest is a process of inferring the behavior of a real hydrocarbon-bearing reservoir from the performance of a numerical model of that reservoir. The objective of reservoir simulation is to understand the complex chemical, physical, and fluid flow processes occurring in the reservoir sufficiently well to predict future behavior of the reservoir to maximize hydrocarbon recovery. Reservoir simulation often refers to the hydrodynamics of flow within a reservoir, but in a larger sense reservoir simulation can also refer to the total petroleum system which includes the reservoir, injection wells, production wells, surface flowlines, and surface processing facilities.

The principle of numerical simulation is to numerically solve equations describing a physical phenomenon by a computer. Such equations are generally ordinary differential equations and partial differential equations. These equations are typically solved using numerical methods such as the finite difference method, the finite element method, and the finite volume method among others. In each of these methods, the physical system to be modeled is divided into smaller cells (a set of which is called a grid or mesh), and the state variables continuously changing in each cell are represented by sets of values for each cell. An original differential equation is replaced by a set of algebraic equations to express the fundamental principles of conservation of mass, energy, and/or momentum within each smaller unit or cells and of mass, energy, and/or momentum transfer between cells. These equations can number in the millions. Such replacement of continuously changing values by a finite number of values for each cell is called "discretization". In order to analyze a phenomenon changing in time, it is necessary to calculate physical quantities at discrete intervals of time called timesteps, irrespective of the continuously changing conditions as a function of time. Time-dependent modeling of the transport processes proceeds in a sequence of timesteps.

In a typical simulation of a reservoir, solution of the primary unknowns, typically pressure and phase saturation or composition, are sought at specific points in the domain of interest. Such points are called "gridnodes" or more commonly "nodes." Cells are constructed around such nodes, and a grid is defined as a group of such cells. The properties such as porosity and permeability are assumed to be constant inside a cell. Other variables such as pressure and phase saturation are specified at the nodes. A link between two nodes is called a "connection." Fluid flow between two nodes is typically modeled as flow along the connection between them.

In conventional reservoir simulation, most grid systems are structured. That is, the cells have similar shape and the same number of sides or faces. Most commonly used structured grids are Cartesian or radial in which each cell has four sides in two dimensions or six faces in three dimensions. While structured grids are easy to use, they lack flexibility in adapting to changes in reservoir and well geometry and often can not effectively handle the spatial variation of physical properties of rock and fluids in the reservoir. Flexible grids have been proposed for use in such situations where structured grids are not as effective. A grid is called flexible or unstructured when it is made up of polygons (polyhedra in three dimensions) having shapes, sizes, and number of sides or faces that can vary from place to place. Unstructured grids can conform to complex reservoir features more easily than structured grids and for this reason unstructured grids have been proposed for use in reservoir modeling.

One type of flexible grid that can be used in reservoir modeling is the Voronoi grid. A Voronoi cell is defined as the region of space that is closer to its node than to any other node, and a Voronoi grid is made of such cells. Each cell is associated with a node and a series of neighboring cells. The Voronoi grid is locally orthogonal in a geometrical sense; that is, the cell boundaries are normal to lines joining the nodes on the two sides of each boundary. For this reason, Voronoi grids are also called perpendicular bisection (PEBI) grids. A rectangular grid block (Cartesian grid) is a special case of the Voronoi grid. The PEBI grid has the flexibility to represent widely varying reservoir geometry, because the location of nodes can be chosen freely. PEBI grids are generated by assigning node locations in a given domain and then generating cell boundaries in a way such that each cell contains all the points that are closer to its node location than to any other node location. Since the inter-node connections in a PEBI grid are perpendicularly bisected by the cell boundaries, this simplifies the solution of flow equations significantly. For a more detailed description of PEBI grid generation, see Palagi, C. L. and Aziz, K.: "Use of Voronoi Grid in Reservoir Simulation," paper SPE 22889 presented at the 66th Annual Technical Conference and Exhibition, Dallas, Tex. (Oct. 6–9, 1991).

The mesh formed by connecting adjacent nodes of PEBI cells is commonly called a Delaunay mesh if formed by triangles only. In a two-dimensional Delaunay mesh, the reservoir is divided into triangles with the gridnodes at the vertices of the triangles such that the triangles fill the reservoir. Such triangulation is Delaunay when a circle passing through the vertices of a triangle (the circumcenter) does not contain any other node inside it. In three-dimensions, the reservoir region is decomposed into tetrahedra such that the reservoir volume is completely filled. Such a triangulation is a Delaunay mesh when a sphere passing through the vertices of the tetrahedron (the circumsphere) does not contain any other node. Delaunay triangulation techniques are well known; see for example U.S. Pat. No. 5,886,702 to Migdal et al.

Through advanced reservoir characterization techniques, it is common to model the geologic structure and stratigraphy of a reservoir with millions of grid cells, each populated with a reservoir property that includes, but is not limited to, rock type, porosity, permeability, initial interstitial fluid saturation, and relative permeability and capillary pressure functions. However, reservoir simulations are typically performed with far fewer grid cells. The direct use of fine-grid models for reservoir simulation is not generally feasible because their fine level of detail places prohibitive demands on computational resources. Therefore, a method is needed to transform or to scale up the fine-grid geologic reservoir model to a coarse-grid simulation model while preserving, as much as possible, the fluid flow characteristics of the fine-grid model.

One key fluid flow property for reservoir simulation is permeability. Permeability is the ability of a rock to transmit fluids through interconnected pores in the rock. It can vary substantially within a hydrocarbon-bearing reservoir. Typically, permeabilities are generated for fine-scale models (geologic models) using data from well core samples. For simulation cells, the heterogeneities of the geologic model are accounted for by determining an effective permeability. An effective permeability of a heterogeneous medium is typically defined as the permeability of an equivalent homogeneous medium that, for the same boundary conditions, would give the same flux (amount of fluid flow across a given area per unit time). Determining an effective permeability, commonly called permeability upscaling, is not straightforward. The main difficulty lies in the interdependent influences of permeability heterogeneities in the reservoir and the applied boundary conditions.

Many different upscaling techniques have been proposed. Most of these techniques can be characterized as (1) direct methods or (2) flow-based methods. Examples of direct methods are simple averaging of various kinds (e.g., arithmetic, geometric and harmonic averaging) and successive renormalization. The flow-based techniques involve the solution of flow equations and account for spatial distribution of permeability. In general, the flow-based methods require more computational effort but are more accurate than the direct methods.

An overview of different upscaling techniques is provided in the following papers: Wen, X. H. and Gomez-Hernandez, J. J., "Upscaling Hydraulic Conductivities in Heterogeneous Media: An Overview," *Journal of Hydrology*, Vol. 183 (1996) 9–32; Begg, S. H.; Carter, R. R. and Dranfield, P., "Assigning Effective Values to Simulator Gridblock Parameters for Heterogeneous Reservoirs," SPE Reservoir Engineering (November 1989) 455–465; Durlofsky, L. J., Behrens, R. A., Jones, R. C., and Bernath, A., "Scale Up of Heterogeneous Three Dimensional Reservoir Descriptions," Paper SPE 30709 presented at the Annual Technical Conference and Exhibition, Dallas, Tex. (Oct. 22–25, 1995); and Li, D., Cullick, A., Lake, L. W., "Global Scale-up of Reservoir Model Permeability with Local Grid Refinement", *Journal of Petroleum Science and Engineering*, Vol. 14 (1995) 1–13. The upscaling techniques proposed in the past were primarily focused on structured grids. A need exists for a method of upscaling permeabilities associated with a fine-scale geologic model to permeabilities associated with an unstructured, coarse-scale reservoir simulation model.

SUMMARY

A method is provided for scaling up permeabilities associated with a fine-scale grid of cells representative of a porous medium to permeabilities associated with an unstructured coarse-scale grid of cells representative of the porous medium. The first step is to generate an areally unstructured, Voronoi, computational grid using the coarse-scale grid as the genesis of the computational grid. The cells of the computational grid are smaller than the cells of the coarse-scale grid and each cell of the computational grid and the coarse-scale grid has a node. The computational grid is then populated with permeabilities associated with the fine-scale grid. Flow equations, preferably single-phase, steady-state pressure equations, are developed for the computational grid, the flow equations are solved, and inter-node fluxes and pressure gradients are then computed for the computational grid. These inter-node fluxes and pressure gradients are used to calculate inter-node average fluxes and average pressure gradients associated with the coarse-scale grid. The inter-node average fluxes and average pressure gradients associated with the coarse grid are then used to calculate upscaled permeabilities associated with the coarse-scale grid.

In a preferred embodiment, the computational grid is constructed from the coarse-scale grid to produce inter-node connections of the computational grid that are parallel to the inter-node connections of the coarse-scale grid. The cells of the computational grid are preferably approximately the same size as the fine-scale cells. The computational grid is preferably populated with permeabilities by assigning to a given node of the computational grid, a predetermined permeability of a cell of the fine-scale grid that would contain the given node's location if the computational grid were superimposed on the fine-scale grid. The flow equations that are developed for the computational grid are preferably single-phase, steady-state equations. The inter-node average fluxes and average pressure gradients associated with the coarse-scale grid are preferably calculated using only the inter-node connections of the computational grid that fall within a predetermined sub-domain of the computational grid, and more preferably such calculations are made using only the inter-node connections of the computational grid that are parallel to the inter-node connection of the coarse-scale grid associated with the subdomain. The permeabilities associated with inter-node connections of the coarse-scale grid are preferably determined by calculating the ratio of the inter-node average fluxes to the inter-node average pressure gradients that were calculated for the coarse-scale grid.

BRIEF DESCRIPTION OF THE DRAWINGS

The present invention and its advantages will be better understood by referring to the following detailed description and the following drawings in which like elements are given like numerals and letters.

The drawings illustrate specific embodiments of practicing the method of this invention. The drawings are not intended to exclude from the scope of the invention other embodiments that are the result of normal and expected modifications of the specific embodiments.

DETAILED DESCRIPTION OF THE INVENTION

This invention provides a flow-based method for upscaling permeabilities associated with a fine-scale, geologic grid system representative of a porous medium to estimated permeabilities associated with a coarse-scale, unstructured grid system representative of the same porous medium. The invention is particularly useful in upscaling permeabilities associated with a geologic model of a reservoir, typically represented by structured cells, to permeabilities associated with a coarse-scale, unstructured, Voronoi grid (also known as perpendicular-bisection or PEBI grid).

As a first step in carrying out the scale-up method, an areally, unstructured, Voronoi grid (often referred to herein as a "computational grid") is generated using the coarse grid as its genesis. In accordance with the practice of this invention, the inter-node connections of both the coarse grid and computational grid are aligned (parallel) with each other. The computational grid is then populated with permeabilities from the fine-scale, geologic grid. The next step is to set up flow equations, preferably single-phase, steady-state pressure equations, for the unstructured computational grid, solve the flow equations, and compute inter-node fluxes and pressure gradients for the computational grid. These fluxes and pressure gradients are then used to calculate inter-node average fluxes and average pressure gradients associated with the coarse grid. Permeabilities associated with the coarse-grid connections are then calculated using the average fluxes and average pressure gradients calculated earlier for the coarse grid.

One embodiment of the invention will now be described with reference to the drawings. Although the drawings illustrate only two-dimensional (2-D) grid systems, this invention is not limited to 2-D grids. As discussed later herein, the invention can also be applied to three-dimensional (3-D) grids.

Figure 1:
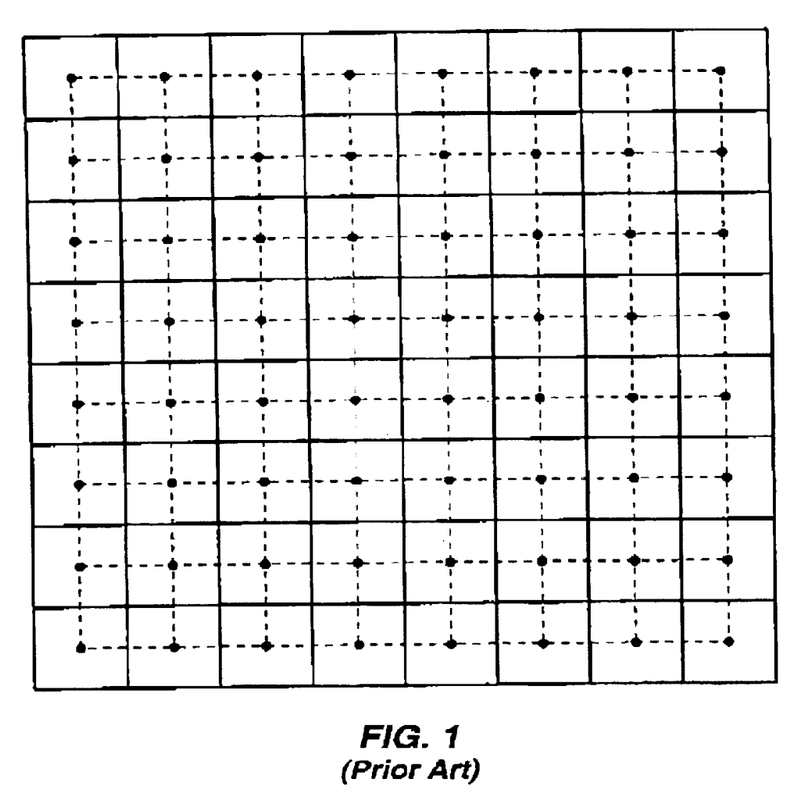
FIG. 1 illustrates a two-dimensional, structured, fine-scale grid commonly used in geologic modeling of a porous medium.

FIG. 1 illustrates an example of a fine-scale, geologic grid for use in representing a porous medium such as an aquifer or hydrocarbon-bearing reservoir. While FIG. 1 shows an 8×8 Cartesian grid of 64 cells, it should be understood that a typical geologic grid could contain millions of cells. All of the cells in FIG. 1 are structured, which is typical of geologic grids, with each cell having a node at its center. In FIG. 1, and in the other drawings, the thick dots denote cell nodes; the continuous lines denote the boundaries of cells; and in FIGS. 1–5 and 7 the dashed lines between nodes are referred to as inter-node connections. The triangles formed by the dashed lines in these figures form Delaunay meshes.

Figure 2:
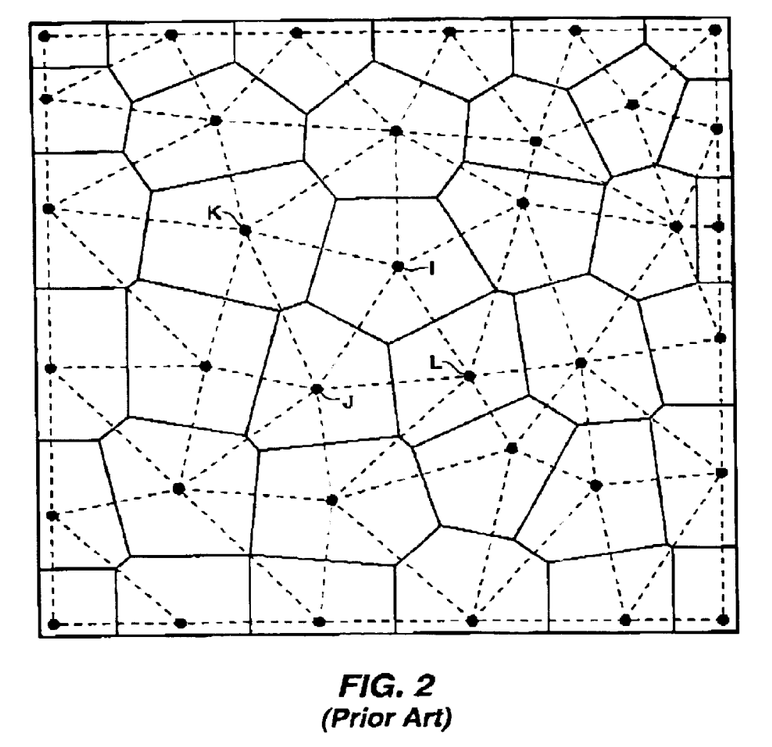
FIG. 2 illustrates a two-dimensional, unstructured, coarse-scale grid having 36 cells of which four cells are shown having nodes designated I, J, K and L.

FIG. 2 illustrates an example of an unstructured, PEBI grid system containing coarse-scale cells suitable for use in reservoir simulation. The grids of FIGS. 1 and 2 represent the same domain of a porous medium. In most reservoir simulation applications, the average size of the coarse-scale cells of FIG. 2 would be several times larger than the average size of fine-scale cells of FIG. 1. A reservoir simulation model may for example involve from about 10 to 1000 geologic cells for each reservoir simulation cell, with the length scale changing from 10 meters or more in the geologic model to 100 meters or more in the reservoir simulation model. Although the cells depicted in FIG. 1 are smaller than the cells depicted in FIG. 2 (for sake of clarity in presentation) they could be even smaller in actual cases. Techniques for generating both fine-scale, geologic grids and coarse-scale simulation grids are well known. The inventors have discovered an effective flow-based upscaling method for transforming the permeabilities associated with the fine-scale grid (such as a structured grid of FIG. 1) to an unstructured, coarse-grid system (such as an unstructured grid of FIG. 2).

Figure 3:
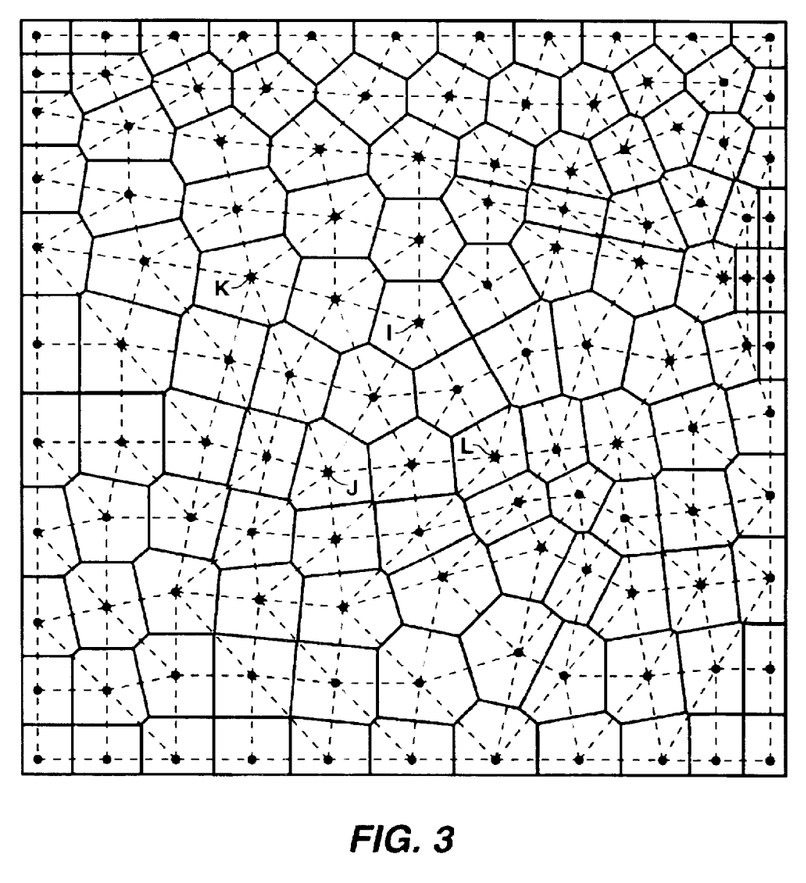
FIG. 3 illustrates a two-dimensional, unstructured computational grid generated from the coarse-scale grid of FIG. 2; the cells of the computational grid were generated using a grid-refinement ratio of 2.

FIG. 3 illustrates one example of a computational grid generated in the practice of this invention that can be used in upscaling the permeabilities from a geologic model of FIG. 1 to an unstructured reservoir simulation model of FIG. 2. The first step in the method of this invention is to generate a computational grid for the same domain covered by FIGS. 1 and 2.

The computational grid is generated in such a way as to produce unstructured, PEBI cells that are smaller than the coarse-grid cells. Each inter-node connection of the computational grid is parallel to an inter-node connection of the coarse grid. As will be discussed in more detail below with respect to the preferred embodiment, this parallel alignment facilitates the upscaling of pressure gradients and fluxes which is an important step in the method of this invention.

The computational grid is generated by assigning nodes in addition to nodes of the coarse-grid and regenerating PEBI cells. The additional nodes are assigned proportionally on all coarse-grid connections and within each Delaunay triangle. The same number of new nodes is added to each connection and any number of new nodes may be added. Increasing the number of nodes increases the number of smaller PEBI cells that can be formed from the coarse-grid cells. Increasing the number of smaller cells of the computational grid is referred to herein as increasing the refinement. The degree of refinement can be measured by counting the number of additional nodes per coarse-grid connection. If one node is added per coarse-grid connection, the refinement ratio is 2 since it divides the coarse-grid connection into two equal minigrid connections; if 2 nodes are added per coarse-grid connection, the refinement ratio is 3, and if 3 nodes are added, the refinement ratio is 4, and so on.

The PEBI grid of FIG. 3 was generated with a refinement ratio of 2. Referring to FIG. 3, nodes I, J, and K represent nodes of the three cells illustrated in FIG. 2 having nodes I, J, and K. To generate the grid of FIG. 3, one additional node was introduced midway between nodes K and I, one additional node was introduced midway between nodes K and J, and one additional node was introduced midway between nodes I and J, and so on for all other inter-node connections of FIG. 2. The PEBI grid of FIG. 3 was then generated based on the original nodes of FIG. 2 and the newly added nodes.

Figure 4:
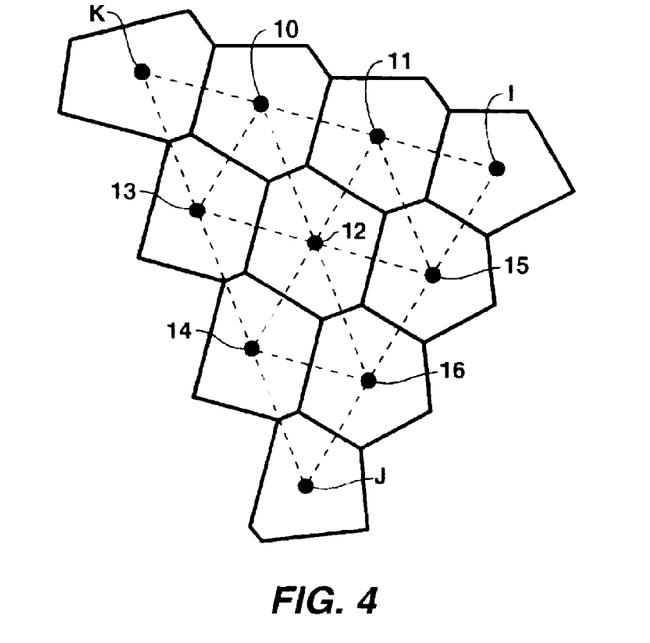
FIG. 4 illustrates 10 unstructured cells generated in the practice of this invention from three unstructured cells of FIG. 2 having nodes I, J, and K; such 10 cells were generated from the three cells using a grid-refinement ratio of 3.
Figure 5:
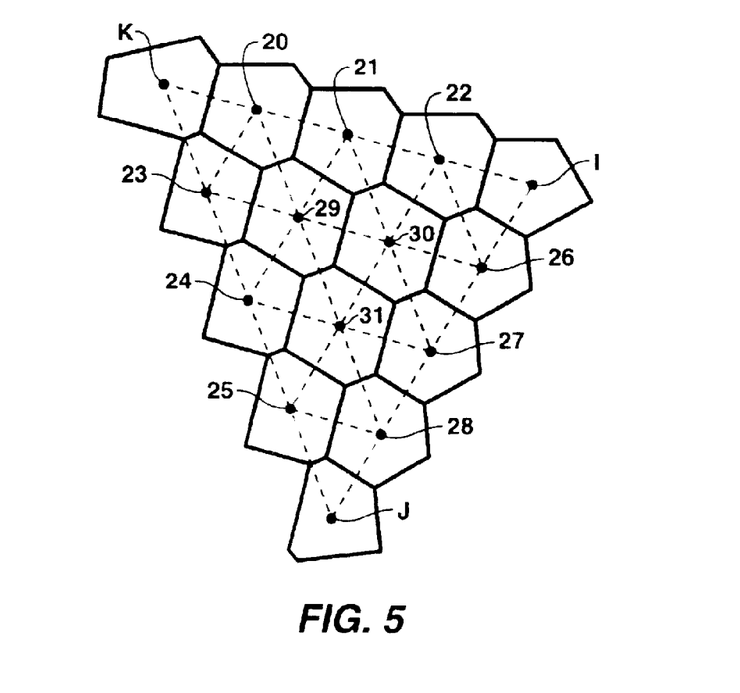
FIG. 5 illustrates 15 unstructured cells generated in the practice of this invention from the three unstructured cells of FIG. 2 having nodes I, J, and K; such 15 cells were generated from the three cells using a grid-refinement ratio of 4.

Examples of computational grids having refinement ratios of 3 and 4 are shown in FIGS. 4 and 5, respectively. FIG. 4 shows 10 PEBI cells generated from the three cells of FIG. 2 having nodes I, J, and K, representing a refinement ratio of 3. To generate the PEBI cells of FIG. 4, two nodes 10 and 11 were added proportionately between nodes K and I; two nodes 13 and 14 were added proportionately between nodes K and J; two nodes 15 and 16 were added proportionately between I and J; and one node 12 was introduced within the triangle formed by node K, 1, and J. The Delaunay mesh (the dashed lines) formed by inter-node connections of the 10 cells of FIG. 4 consists of 9 equal-sized Delaunay triangles having equal angles. All 9 smaller Delaunay triangles of FIG. 4 are similar to the Delaunay triangle IJK of FIG. 2.

FIG. 5 shows 15 PEBI cells generated from the three cells of FIG. 2 having nodes I, J, and K, representing a refinement ratio of 4. To generate the 15 PEBI cells shown in FIG. 5, three nodes 20, 21, and 22 were added proportionately between nodes K and I of FIG. 2; three nodes 23, 24, and 25 were added proportionately between nodes K and J; three nodes 26, 27, and 28 were added proportionately between I and J; and three nodes 29, 30, and 31 were proportionately added within the triangle formed by node K, I, and J. Nodes 29, 30, and 31 lie at the intersections of lines drawn parallel to sides of triangle KIJ through nodes 20–28. Hence, all inter-node connections of the PEBI cells in FIG. 5, are parallel to one of the inter-node connections between nodes K and I, between nodes K and J, and nodes I and J of FIG. 2. For example, referring to FIG. 5, the inter-node connection between nodes 20 and 23 is parallel to the inter-node connection between I and J of FIG. 2; the inter-node connection between nodes 23 and 24 is parallel to the inter-node connection between nodes K and J of FIG. 2; and the inter-node connection between nodes 29 and 30 is parallel to the inter-node connection between nodes K and I of FIG. 2.

For a given refinement ratio, the number of similar, smaller, Delaunay triangles of a computational grid that can be produced is $n^2$ times the number of Delaunay triangles of the coarse-scale grid, where n is a desired integer refinement ratio. For example, a computational grid with a refinement ratio of 4 will have sixteen ($4^2$) Delaunay triangles (the Delaunay grid of FIG. 5) that are similar to, and smaller than, the Delaunay triangle KIJ of FIG. 2.

The refinement ratio can be any integer greater than 1. For most reservoir simulation applications, as a non-limiting example, the refinement ratio may range from 2 to about 10, and more typically the ratio will range from 2 to 5. The desired refinement ratio will depend on the relative sizes of the geologic grid and the coarse grid and the desired number of computational grid cells. The refinement ratio is preferably chosen to generate computational grid cells of approximately the same size as cells of the geologic grid for the same domain of the reservoir, and more preferably the refinement ratio chosen produces computational grid cells slightly smaller than the geologic cells.

The method of this invention generates PEBI cells when all angles of each Delaunay-mesh triangle form coarse-grid connections that are smaller than 90° (acute triangle) or when one angle is at most equal to 90° (right triangle). However, if any angle of a Delaunay triangle is greater than 90° (obtuse triangle), a true perpendicular bisector does not exist. For such triangles, the grid-generation technique of this invention will produce connections that are not parallel to the overlying coarse-grid connections. If any such non-parallel connections are generated, they are preferably not used in upscaling permeabilities from the computational grid to the coarse-grid as discussed in more detail below. The coarse-grid is preferably generated such that there are no obtuse triangles in the Delaunay-mesh. This can be achieved by adjusting node locations in most situations.

The minigrid-generation technique of this invention is not limited to a triangular connection mesh (Delaunay-mesh); it is also applicable to structured grids in which the connection mesh comprises rectangles. The present computational grid generation technique is also applicable to a connection mesh that comprises a combination of triangles and rectangles.

Permeability Population

Once the computational grid has been generated, the next step in the method of this invention is to populate permeabilities onto the computational grid. This populating step is carried out using predetermined permeabilities associated with the fine-scale, geologic model (FIG. 1 for example). Various populating approaches can be used. One approach assigns permeabilities from the geologic grid to nodes of the computational grid as follows. For a given node on the computational grid, the geologic grid is searched until the cell of the geologic grid is located that contains the node of the computational grid, assuming that the computational grid is superimposed on the geologic grid. The predetermined permeability of the geologic cell that contains a given node of the computational grid is assigned as the permeability of that given node. Each inter-node connection permeability of the computational grid is then computed by averaging (preferably by harmonic averaging) the two node permeabilities forming the inter-node connection. Another approach to populating the computational grid with permeabilities is to assign to the midpoints of the computational grid's inter-node connections, permeabilities obtained from the geologic cells. For a given midpoint of the computational grid's inter-node connection, a cell of the geologic grid is located that contains the given mid-point (assuming that the computational grid is superimposed on the geologic grid) and the permeability of that geologic cell is assigned to the given midpoint. If the geologic model has a diagonal permeability tensor, the two areal permeabilities can be combined based on the connection direction, before population.

Fluid Flow Equations

After the computational grid has been populated with permeabilities, the next step in the practice of this invention is to develop flow equations for the computational grid, preferably single-phase, steady-state pressure equations for each cell of the computational grid, and using an assumed set of boundary conditions, solve the equations for each computational grid cell. The single-phase, steady-state pressure equation is given as:

$$\nabla \cdot \bar{\bar{k}} \nabla P = 0 \qquad (1)$$

where P is pressure and $\bar{\bar{k}}$ is the permeability tensor.

The following description makes use of mathematical symbols, many of which are defined as they occur throughout the text. Additionally, for purposes of completeness, a symbols table containing definitions of symbols used herein is presented following the detailed description.

Assuming, but not limited to, a scalar connection permeability, the discretized form of Eq. (1) for PEBI grids is:

$$\sum_l T_{lj}(P_j - P_l) = 0 \qquad (2)$$

where T is transmissibility, subscript j refers to the node of interest and subscript l refers to all of its neighbors. The term transmissibility as used in this description refers to a measure of the capability of a given viscosity fluid to move across a cell boundary (or inter-node connection) under a pressure drop. More specifically, transmissibility is known to those skilled in the art as a measure of the ability of a fluid to flow between two neighboring cells within a porous medium. Transmissibility is expressed as $$\frac{kA}{\Delta s},$$

where k is the effective permeability of the porous medium, A is the area of the boundary between the neighboring cells, and Δs is the average or characteristic distance that the fluid must travel in moving between the two cells.

Figure 6:
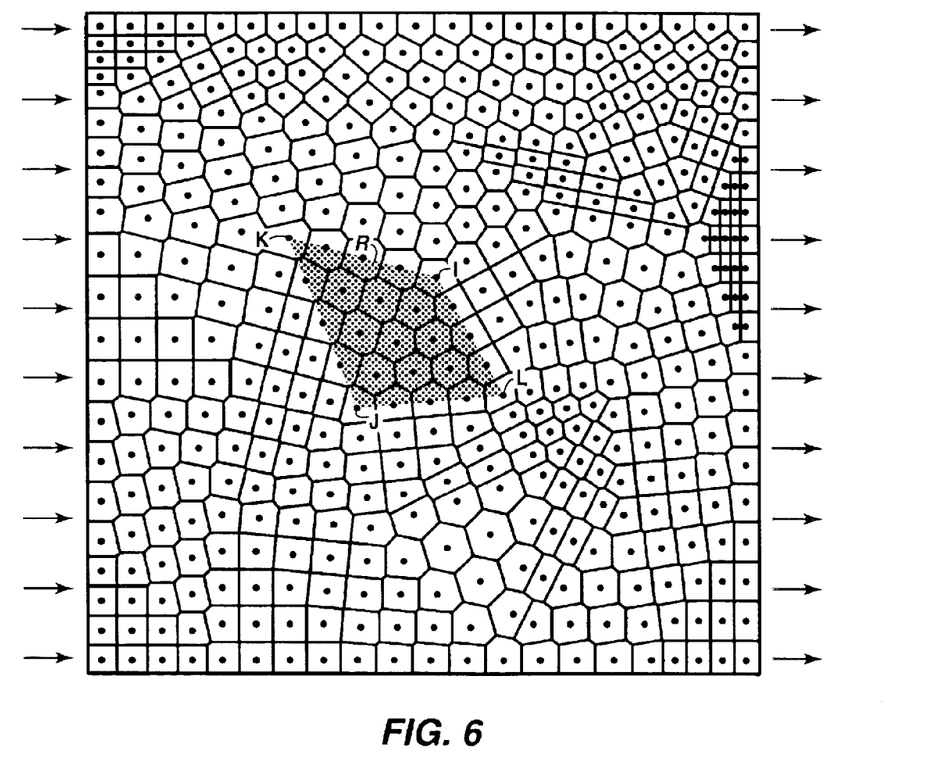
FIG. 6 illustrates a two-dimensional computational grid generated from the grid of FIG. 2 using a grid-refinement ratio of 4, and shows a diamond shaped sub-domain KILJ.

One acceptable set of boundary conditions exerts a constant pressure gradient in the flow direction and assumes no flow in the transverse direction (no-transverse-flow boundary conditions). As shown in FIG. 6, fluid flow is assumed to be injected or produced only in the direction of the arrows (from left to right). Another set of boundary conditions suitable for the practice of this invention is linear boundary conditions. In linear boundary conditions, a constant pressure gradient is applied in the flow direction along all boundaries. This can result in flow across all boundaries which can help in upscaling permeabilities in isolated areas. The foregoing boundary conditions should not be construed as limitation of the invention; other suitable boundary conditions can also be used.

The pressure equation is solved in each of the two principal directions for 2-D applications (and in three principal directions for 3-D applications). Fluxes and pressure gradients are then computed for all inter-node connections of the computational grid. Persons skilled in the art of reservoir simulation would be familiar with development of suitable single-phase pressure equations for each cell of the computational grid, solving the pressure equations, and computing fluxes and pressure gradients for all inter-node connections of the computational grid. See for example, Verma, S., "A Control Volume Scheme for Flexible Grids in Reservoir Simulation," paper SPE 37999 presented at the Reservoir Simulation Symposium, Dallas Tex. (Jun. 8–11, 1997).

Upscaling

Once the fluxes and pressure gradients computed are determined for the computational grid, the average fluxes and average pressure gradients associated with connections of the coarse grid are computed. These pressure gradients and fluxes are averaged over predetermined integration sub-domains associated with each coarse-grid cell, preferably sub-domains associated with each inter-node connection of the coarse grid. The ratio of the upscaled flux to upscaled pressure gradient then gives the upscaled permeability. This upscaled permeability can then be used to compute transmissibility.

A mathematical basis for upscaling permeabilities from a computational grid to the coarse grid will now be provided. This description makes use of several mathematical symbols, some of which are defined as they occur in this description. Additionally, for purposes of completeness, a symbols table containing definitions of symbols used herein is presented following the detailed description.

Darcy's law for 1-D single-phase flow in direction s is given by:

$$u = -\frac{k}{\mu}\frac{\partial P}{\partial s} \qquad (3)$$

Integrating Eq. (3) with respect to volume for computing an average flux over the volume of sub-domain R gives:

$$\frac{1}{V_R}\int_{V_R} u\, dV = -\frac{1}{V_R}\int_{V_R} \frac{k}{\mu}\left(\frac{\partial P}{\partial s}\right) dV \qquad (4)$$

Assuming constant viscosity, the upscaled permeability ($\bar{k}$) for sub-domain R in direction s at the coarse-scale grid can now be defined as:

$$-\frac{1}{\mu}\frac{1}{V_R}\int_{V_R}k\left(\frac{\partial P}{\partial s}\right)dV = -\frac{\bar{k}}{\mu}\frac{1}{V_R}\int_{V_R}\left(\frac{\partial P}{\partial s}\right)dV \quad (5)$$

Equation (5) can be expressed as a ratio of upscaled flux to upscaled pressure gradient by the following relationship, which was described in a paper by Rubin, Y. and Gomez-Hernandez, J. J., "A Stochastic Approach to the Problem of Upscaling of Conductivity in Disordered Media: Theory and Unconditional Numerical Simulations," *Water Resources Research*, Vol. 26, No. 4, pages 691–701, April, 1990:

$$\bar{k} = \frac{\int_{V_R}k\left(\frac{\partial P}{\partial s}\right)dV}{\int_{V_R}\left(\frac{\partial P}{\partial s}\right)dV} \quad (6)$$

Approximating the integrals in Eq. (6) on the fine scale and substituting connection volume $V_f(V_f=A_f\Delta s_f)$, the following expression for upscaled permeability ($k_c$) is obtained:

$$k_c \approx \frac{\sum_i k_{fi}\left(\frac{\Delta P_f}{\Delta s_f}\right)_i V_{fi}}{\sum_i \left(\frac{\Delta P_f}{\Delta s_f}\right)_i V_{fi}} = \frac{\sum_i A_{fi}\Delta P_{fi}k_{fi}}{\sum_i A_{fi}\Delta P_{fi}} \quad (7)$$

The connection transmissibility can now be computed as:

$$T_c = \frac{k_c A_c}{\Delta s_c} \quad (8)$$

Equation (7) can be applied using pressure gradients and fluxes computed from the pressure equation solution on the PEBI computational grid. An important step is to determine a sub-domain or region of integration associated with each coarse-grid connection over which the computational grid permeabilities are to be upscaled.

Figure 7:
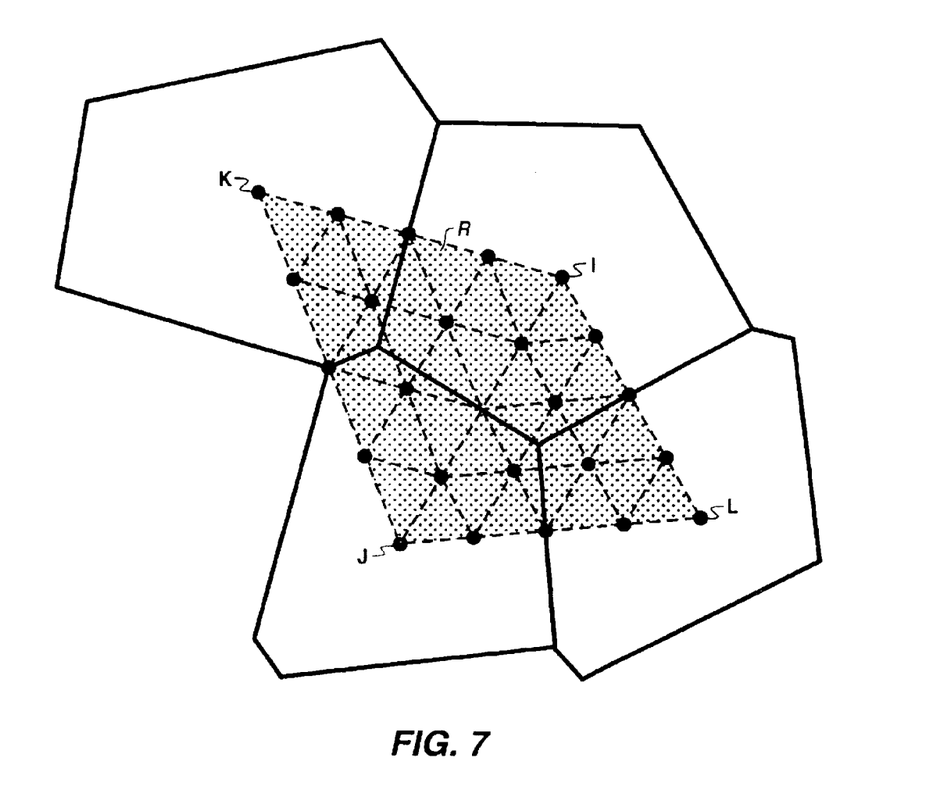
FIG. 7 illustrates four coarse-grid cells of FIG. 2 having nodes I, J, K, and L and the diamond shaped sub-domain R of FIG. 6.

Referring to FIGS. 6 and 7, for upscaling areal connection permeabilities on PEBI grids, a suitable sub-domain is a diamond-shaped sub-domain R consisting of two triangles (KIJ and IJL) of FIG. 2. Other suitable sub-domain shapes can also be used. Equation (7) can now be used to compute upscaled permeability for each sub-domain using part or all of the computational grid's inter-node connections within the sub-domain using a predetermined selection criterion. In a simple but efficient approach, the upscaled permeability uses only the inter-node connections of the computational grid within sub-domain R that are parallel to the coarse-grid's inter-node connection representative of sub-domain R. In another embodiment, all of the computational grid's inter-node connections in sub-domain R could be used in the upscaling.

Referring to FIG. 7, the computational grid inter-node connections in sub-domain R are used to obtain an upscaled permeability for the inter-node connection between nodes I and J. Since the pressure equation is solved in two principal directions in the areal domain, two upscaled permeabilities are obtained. If no-transverse-flow boundary conditions are used, the final upscaled permeability is selected based on the areal direction with the highest average pressure gradient for each coarse-grid areal connection. Other techniques could be applied to upscale the permeabilities using combinations of the two pressure equation solutions. For example, when linear boundary conditions are used, a linear combination of the two pressure gradients can be obtained as follows:

$$\frac{\partial P}{\partial s} = a\left(\frac{\partial P}{\partial s}\right)_1 + b\left(\frac{\partial P}{\partial s}\right)_2 \quad (9)$$

Constants a and b are determined such that the resulting pressure gradient is aligned with the connection direction for which the permeability is to be upscaled. The upscaled permeability now can be expressed as:

$$\bar{k} = \frac{\int_{V_R}k\left[a\left(\frac{\partial P}{\partial s}\right)_1 + b\left(\frac{\partial P}{\partial s}\right)_2\right]dV}{\int_{V_R}\left[a\left(\frac{\partial P}{\partial s}\right)_1 + b\left(\frac{\partial P}{\partial s}\right)_2\right]dV} \quad (10)$$

The upscaling technique of this invention can also be applied to 3-D structured as well as 3-D layered PEBI grids (also referred to by some as 2½-D PEBI grids). Extension to 3-D unstructured grids is also possible. The layered PEBI grids are unstructured areally and structured (layered) vertically. One way to create such grids is to project 2-D areal PEBI grids on geologic sequence surfaces. Areal connection permeabilities can be upscaled layer-by-layer or over multiple layers. For upscaling vertical (inter-layer) connection permeabilities, the flow equations would be solved with the pressure gradient in the vertical direction. Construction of layered 3-D grids is described by (1) Heinemann, Z. E., et al., "Modeling Reservoir Geometry With Irregular Grids," *SPE Reservoir Engineering*, May, 1991 and (2) Verma, S., et al., "A Control Volume Scheme for Flexible Grids in Reservoir Simulation," SPE 37999, SPE Reservoir Simulation Symposium, Dallas, Tex., June, 1997. The upscaling method of this invention can also be extended to full 3-D PEBI grids.

Figure 8:
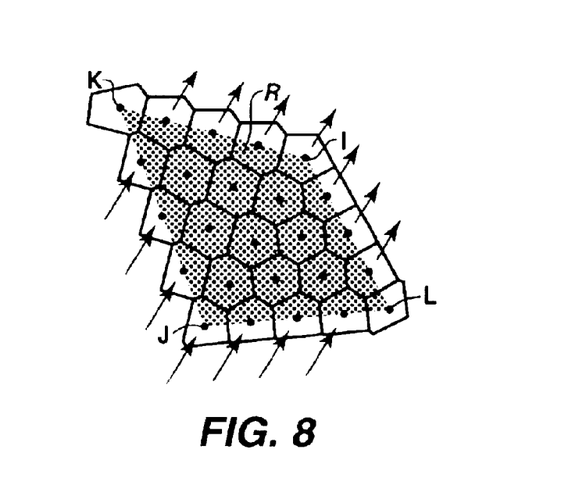
FIG. 8 illustrates a computational grid that is a subdomain of the grid in FIG. 6 and only includes the region of integration R of FIG. 6.

A very useful aspect of this invention is that the scale-up method can be applied to upscale permeabilities for an arbitrary number of coarse-grid connections simultaneously. The fluid flow equations can be solved on a computational grid corresponding to a large coarse-grid domain (scale-up domain), thus permitting a large number of permeabilities to be upscaled at once. For example, the fluid flow equations can be solved for the entire computational grid of FIG. 6 to upscale permeabilities for all the coarse grid inter-node connections shown in FIG. 2. Alternatively, the fluid flow equations can be solved on a smaller computational grid corresponding to one or a few coarse-grid connections. An example of a computational grid for upscaling one coarse-grid connection permeability is shown in FIG. 8. Here, the computational-grid coincides with the diamond-shaped region of integration R used in upscaling permeability for coarse-grid connection IJ.

Figure 9:
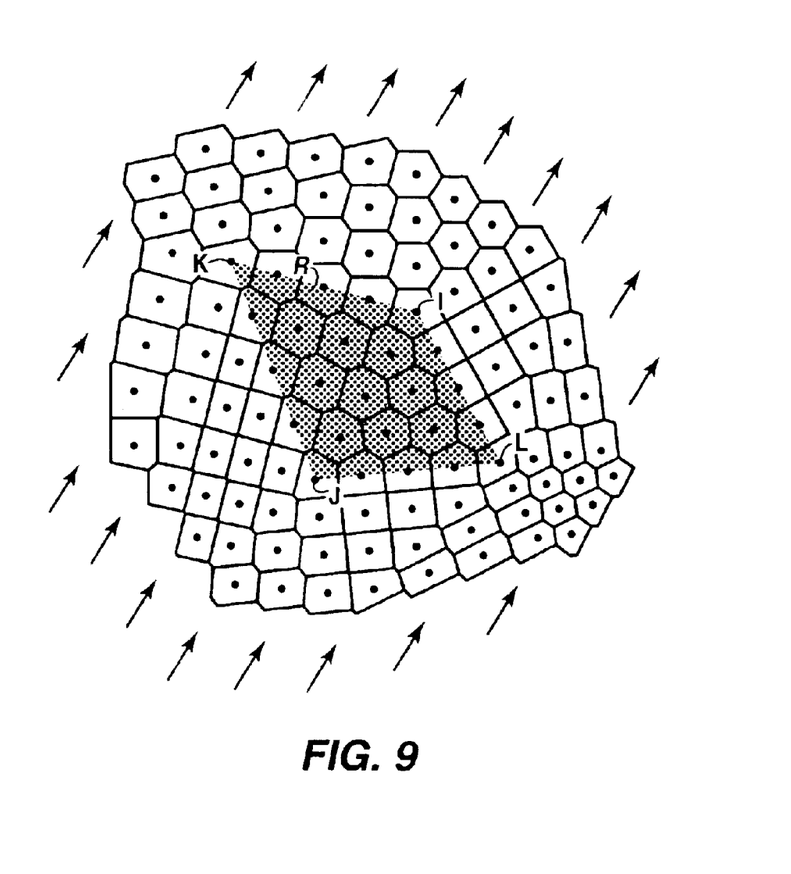
FIG. 9 illustrates a computational grid that is a sub-domain of the grid in FIG. 6, which includes a region of integration R of FIG. 6 and a buffer zone (skin region) around region R.

The flow equations can also be solved on a larger computational grid than the scale-up domain thus allowing a buffer or skin around the scale-up domain whether it consists of single or multiple connections. An example of this is shown in FIG. 9 where the computational grid includes the diamond-shaped region of integration R (KILJ) for connection IJ and a buffer zone or skin region surrounding region R. These options offer flexibility in selecting scale-up domain size as well as computational-grid size for upscaling, which could be important for scale-up accuracy in certain applications where actual field boundary conditions are different from the scale-up boundary conditions.

Although the mathematical description of the upscaling method of this invention has been presented with a single-phase, no gravity, steady-state, scalar permeability formulation, the method by no means is limited to these assumptions. Persons skilled in the art can extend the scale-up method of this invention to include multiphase flow, unsteady state flow, a full permeability tensor, and gravity using the information disclosed in this patent.

Although not shown in the drawings, in practicing the present invention, the properties of the domain being simulated can optionally be visualized on 2-D and 3-D unstructured grids using suitable computerized visualization equipment. The visualization of the properties can be helpful in analyzing application of the invention. In 2-D, a connection property (such as flux, pressure gradient or connection permeability) can be represented by displaying a diamond-shaped region associated with each connection in color from a predefined color scale. The apexes of this diamond-shaped region include the two node locations forming the connection and the end-points of the perpendicular bisector of the connection. In 3-D, the Delaunay triangulation can be represented by a ball and stick network. Node properties (such as pressure, saturation, composition or porosity) can be displayed by coloring the balls using a color scale. Similarly, the connection properties can be displayed by coloring the sticks. The color scale can display the magnitude of a property. For displaying a vector property (for example, pressure gradient or flux), an arrowhead can be used to represent the flow direction.

The principle of the invention and the best mode contemplated for applying that principle have been described. It will be apparent to those skilled in the art that various changes may be made to the embodiments described above without departing from the spirit and scope of this invention as defined in the following claims. It is, therefore, to be understood that this invention is not limited to the specific details shown and described.

SYMBOLS a, b=Constants, dimensionless
A=Area, ft$^2$
k=Permeability, md
k̂=Effective Permeability of Entire Grid Domain, md
P=Pressure, psi
T=Transmissibility, md-ft
u=Darcy Flux, ft/day
V=Volume, ft$^3$
ΔP=Pressure Drop, psi
Δs=Connection Length, ft
$\mu$=Viscosity, cp
Subscripts
c=Coarse Grid
f=Computational Grid
i=Connection Index
j, l=Node Index
R=Sub-domain of Integration

What is claimed is:

1. A method of scaling up permeabilities associated with a fine-scale grid of cells representative of a porous medium to permeabilities associated with an unstructured coarse-scale grid of cells representative of the porous medium, comprising the steps of:
   (a) generating an areally unstructured, Voronoi, computational grid using the coarse-scale grid as the genesis of the computational grid, the cells of the computational grid being smaller than the cells of the coarse-scale grid and each cell of said computational grid and said coarse-scale grid having a node;
   (b) populating the computational grid with permeabilities associated with the fine-scale grid;
   (c) developing flow equations for the computational grid, solving the flow equations, and computing inter-node fluxes and pressure gradients for the computational grid;
   (d) using the fluxes and pressure gradients computed in step (c) to calculate inter-node average fluxes and average pressure gradients associated with the coarse-scale grid; and
   (e) calculating upscaled permeabilities associated with the coarse-scale grid using the average fluxes and average pressure gradients calculated in step (d).

2. The method of claim 1 wherein inter-node connections of the computational grid cells are parallel to inter-node connections of the coarse-scale grid.

3. The method of claim 1 wherein cells of the computational grid are approximately the same size as the cells of the fine-scale grid.

4. The method of claim 1 wherein cells of the computational grid are smaller than the cells of the fine-scale grid.

5. The method of claim 1 wherein the permeabilities populated in step (b) are assigned to nodes of the computational grid, the permeability assigned to a given node of the computational grid corresponding to a predetermined permeability of a cell of the fine-scale grid that would contain the given node's location if the computational grid was superimposed on the fine-scale grid.

6. The method of claim 5 further comprises calculating the permeability for a given inter-node connection of the computational grid by harmonically averaging the permeabilities at the two nodes forming the given inter-node connection.

7. The method of claim 1 wherein the permeabilities populated in step (b) are assigned to midpoints of a given inter-node connection of the computational grid, the permeability assigned to the given inter-node connection corresponding to a predetermined permeability of a cell of the fine-scale grid that would contain the mid-point of such inter-node connection if the computational grid was superimposed on the fine-scale grid.

8. The method of claim 1 wherein the calculation of the inter-node average fluxes and average pressure gradients in step (d) is determined by using only the fluxes and pressure gradients computed for the inter-node connections of the computational grid that fall within a predetermined sub-domain of the computational node.

9. The method of claim 1 wherein the calculation of the average fluxes and average pressure gradients in step (d) for a given inter-node connection of the coarse-scale grid is determined using only fluxes and pressure gradients computed in step (c) for the inter-node connections of the computational grid that are parallel to the given inter-node connection.

10. The method of claim 1 wherein the permeabilities calculated in step (e) are determined for a given node of the coarse-scale grid.

11. The method of claim 1 wherein the permeabilities calculated in step (e) are determined for a given inter-node connection of the coarse-scale grid by calculating the ratio of the average flux to the average pressure gradient computed in step (d) for the given inter-node connection.

12. The method of claim 1 wherein cells of the fine-scale grid are structured.

13. The method of claim 1 wherein the coarse-scale grid is a PEBI grid.

14. The method of claim 1 wherein both the coarse-scale grid and the computational grid are PEBI grids.

15. The method of claim 1 wherein inter-node connections of the coarse grid forms Delaunay triangles and the computational grid generated in step (a) contains similar, smaller Delaunay triangles equal in number to $n^2$ times the number of Delaunay triangles of the large-scale grid, where n is a predetermined integer refinement ratio used to generate the computational grid.

16. The method of claim 1 wherein all cells are three-dimensional.

17. The method of claim 16 wherein the coarse-scale grid and the computational grid are both unstructured areally and structured vertically.

18. The method of claim 1 further comprises determining inter-node connection transmissibilities of the coarse-scale grid using permeabilities calculated in step (e).

19. The method of claim 1 wherein the flow equations of step (c) are single-phase and steady-state.

20. A method for estimating permeability of each cell of a first grid having a multiplicity of cells of a subterranean geologic domain using a predetermined permeability for each cell of a second grid representative of the domain, said second grid containing a larger number of cells than the first grid, the method comprising:

(a) constructing an unstructured, third grid representative of the domain comprising approximately the same or greater number of cells than the second grid, each cell of the first, second, and third grids having a node and each link between two nodes of adjacent cells being an inter-node connection, substantially all of the inter-node connections of the third grid being parallel to the inter-node connections of the first grid;

(b) for each node of the third grid, assigning a permeability corresponding to the permeability of a cell of the second grid that contains the node location of the third grid;

(c) developing a single-phase, steady-state pressure equation for each cell of the third grid system;

(d) solving the pressure equations and computing fluxes and pressure gradients for all inter-node connections of the third grid;

(e) computing an estimated permeability for a given connection of the first grid using inter-node connections of the third grid; and (f) repeating step (e) for all connections of the first grid.

21. The method of claim 20 further comprises computing the permeability in step (e) by the additional steps of determining average fluxes and average pressure gradients over sub-domains associated with a given grid inter-node connection of the first grid and calculating a ratio of the average flux to the average pressure gradient, thereby obtaining the permeability for the given inter-node connection of the first grid.

22. The method of claim 20 wherein the permeability computation of step (e) uses only inter-node connections of the third grid that are parallel to inter-node connections of the first grid.

23. The method of claim 20 wherein all grid cells are three-dimensional.

24. The method of claim 23 wherein the second grid and the third grid are each unstructured areally and structured vertically.

25. A method for estimating permeabilities associated with cells of a large-scale grid representative of fluid flow in a porous medium using predetermined permeabilities associated with cells of a small-scale grid also representative of fluid flow in the porous medium, each cell of the large-scale grid having a node and each node being linked to adjacent nodes to form inter-node connections and such connections forming Delaunay triangles, comprising the steps of:

(a) constructing a computational grid by dividing each Delaunay triangle of the large-scale grid into a multiplicity of similar, smaller Delaunay triangles, the sides of such smaller Delaunay triangles being inter-node connections of the computational grid and the inter-node connections of the large-scale grid and the computational grid being aligned with each other;

(b) assigning permeabilities to the computational grid corresponding to the predetermined permeabilities of the small-scale grid;

(c) developing a single-phase, steady-state pressure equation for each cell of the computational grid, solving the pressure equations, and computing fluxes and pressure gradients for all inter-node connections of the computational grid;

(d) using the fluxes and pressure gradients computed in step (c) to calculate an average flux and an average pressure gradient for each inter-node connection of the large-scale grid; and (e) calculating a permeability associated with a given inter-node connection of the large-scale grid using the average flux and average pressure gradient calculated in step (d).

26. The method of claim 25 wherein the number of nodes of the computational grid are approximately the same as the number of cells of the small-scale grid.

27. The method of claim 25 wherein the number of nodes of the computational grid are smaller than the number of cells of the small-scale grid.

28. The method of claim 25 wherein the number of similar, smaller Delaunay triangles is $n^2$ times the number of Delaunay triangles of the large-scale grid, where n is a predetermined integer refinement ratio.

* * * * *